US010590447B2

(12) United States Patent
Raemakers-Franken et al.

(10) Patent No.: US 10,590,447 B2
(45) Date of Patent: Mar. 17, 2020

(54) PROCESS FOR THE PREPARATION OF AMMELINE

(71) Applicant: DSM IP ASSETS B.V., Heerlen (NL)

(72) Inventors: Petronella Catharina Raemakers-Franken, Echt (NL); Renier Henricus Maria Kierkels, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 36 days.

(21) Appl. No.: 15/033,949

(22) PCT Filed: Nov. 19, 2014

(86) PCT No.: PCT/EP2014/074967
§ 371 (c)(1),
(2) Date: May 3, 2016

(87) PCT Pub. No.: WO2015/075048
PCT Pub. Date: May 28, 2015

(65) Prior Publication Data
US 2018/0282775 A1 Oct. 4, 2018

(30) Foreign Application Priority Data
Nov. 21, 2013 (EP) .................................... 13193770

(51) Int. Cl.
*C12N 9/14* (2006.01)
*C07C 27/22* (2006.01)
*C12P 17/14* (2006.01)
*C12P 17/12* (2006.01)
*A61K 38/00* (2006.01)

(52) U.S. Cl.
CPC ....... *C12P 17/12* (2013.01); *C12Y 305/04003* (2013.01); *C12Y 305/99003* (2013.01); *C12Y 308/01008* (2013.01)

(58) Field of Classification Search
None
See application file for complete search history.

(56) References Cited

U.S. PATENT DOCUMENTS 5,677,450 A * 10/1997 Suzuki ................. C07D 251/54
544/194
7,704,724 B1 * 4/2010 Fry ........................... C12N 9/80
435/228

2003/0006197 A1 * 1/2003 Mahoney .................. C02F 1/56
210/725
2009/0221014 A1 * 9/2009 Reardon ................ C12Q 1/002
435/18
2011/0008809 A1 1/2011 Krebs
2016/0355667 A1 12/2016 Raemakers-Franken et al.

FOREIGN PATENT DOCUMENTS

WO  WO 01/64912  9/2001

OTHER PUBLICATIONS

Seffernick et al. (2010) X-ray Structure and Mutational Analysis of the Atrazine Chlorohydrolase TrzN, J. Biol. Chem., vol. 285, pp. 30606-30614.*
International Search Report for PCT/EP2014/074967, dated Feb. 11, 2015, 5 pages.
Written Opinion of the ISA for PCT/EP2014/074967, dated Feb. 11, 2015, 6 pages.
Seffernick et al., "Bacterial Ammeline Metabolism via Guanine Deaminase", *Journal of Bacteriology*, vol. 192, No. 4, Dec. 18, 2009, pp. 1106-1112.
Seffernick et al., "Melamine Deaminase and Atrazine Chlorohydrolase: 98 Percent Identical but Functionally Different", *Journal of Bacteriology*, vol. 183, No. 8, Apr. 15, 2001, pp. 2405-2410.
Dodge et al., "Plasmid Localization and Organization of Melamine Degradation Genes in *Rhodococcus* sp. Strain Mel", *Applied and Environmental Microbiology*, vol. 78, No. 5, Dec. 30, 2011, pp. 1397-1403.
Final Office Action issued in U.S. Appl. No. 15/033,954, dated Apr. 11, 2019.
Office Action issued in U.S. Appl. No. 15/033,954, dated Oct. 19, 2018.
Final Office Action issued in U.S. Appl. No. 15/033,954, dated Dec. 15, 2017.
Office Action issued in U.S. Appl. No. 15/033,954, dated Mar. 29, 2017.

* cited by examiner

Primary Examiner — Paul J Holland
Assistant Examiner — Samuel W Liu
(74) Attorney, Agent, or Firm — Nixon & Vanderhye P.C.

(57) ABSTRACT

The present invention relates to a new process for the preparation of ammeline and/or ammelide from melamine by a solid-to-solid reaction in an aqueous reaction mixture comprising a biocatalyst, wherein the biocatalyst comprises at least one enzyme belonging to the amidohydrolase superfamily and having aminohydrolase activity towards 1,3,5-triazine compounds. The invention further relates a product obtainable by the process according to the invention, wherein the product comprises ammeline and/or ammelide.

13 Claims, No Drawings
Specification includes a Sequence Listing.

PROCESS FOR THE PREPARATION OF AMMELINE

This application is the U.S. national phase of International Application No. PCT/EP2014/074967 filed 19 Nov. 2014, which designated the U.S. and claims priority to EP Patent Application No. 13193770.8 filed 21 Nov. 2013, the entire contents of each of which are hereby incorporated by reference.

The present invention relates to a process for the preparation of ammeline and/or ammelide. The invention further relates a product obtainable by the process according to the invention, wherein the product comprises ammeline and/or ammelide.

Ammeline (4,6-diamino-2-hydroxy-1,3,5-triazine) and ammelide (6-amino-2,4-dihydroxy-1,3,5-triazine) are 1,3,5-triazine compounds of industrial interest, e.g. for use in flame retardant compositions as mentioned for example in U.S. Pat. No. 4,341,694, JP55094953, JP59029676. They are however not commercially available on large, industrial scale today.

Several chemical routes have been investigated and described for the preparation of ammeline and ammelide (E. M. Smolin and L. Rapoport. 2008. Ammelide, Ammeline and Related Compounds. In: Chemistry of heterocyclic compounds: s-Triazines and Derivatives. Volume 13. Chapter 5. p. 269-308). Such synthetic routes are quite laborious and troublesome. Furthermore, these require relatively expensive starting materials (e.g. dicyandiamide and biuret), severe reaction conditions (temperatures above 200° C.), halogen-containing compounds, toxic solvents (e.g. phenols, cresols or xylenol), and the addition of alcohols (e.g. methanol) for the precipitation and recovery of the ammeline and/or ammelide from the solvent. Additionally, these routes often lead to formation of ammeline and ammelide in uncontrolled ratios and to limited yields in combination with formation of varying quantities of by-products, e.g. cyanuric acid, of which removal by washing is difficult and expensive due its very low solubility. Accordingly, there is a need for alternative routes to ammeline and/or ammelide, preferably a more cost-effective process from cheap starting materials, such as melamine (2,4,6-triamino-1,3,5-triazine; also called sym-triamino-triazine).

It is an object of the present invention to provide a process for the preparation of ammeline and/or ammelide that would overcome one or more of the drawbacks mentioned above, in particular resulting in a high yield and low amount of by-products, thereby providing a commercially attractive process.

It is also an object of the present invention to provide a novel process for the preparation of ammeline and/or ammelide, wherein the ammeline:ammelide ratio can be fine-tuned.

It is further an object of the present invention to provide a product that comprises ammeline and/or ammelide in a controlled ratio.

These objects have been achieved with the process according to the invention comprising a process for the preparation of ammeline and/or ammelide, wherein melamine is converted into ammeline, and optionally ammelide, by a solid-to-solid reaction in an aqueous reaction mixture comprising a biocatalyst and wherein the biocatalyst comprises at least one enzyme belonging to the amidohydrolase superfamily and having aminohydrolase activity towards 1,3,5-triazine compounds.

In the process according to the invention, melamine is converted into ammeline, and optionally ammelide, by a "solid-to-solid" reaction. This means that in said reaction, only a small proportion of the substrate and/or the product is in solution at any time, while the remainder part of the substrate and/or product is in a solid phase. The starting solid melamine substrate dissolves progressively, passing through solution as it is converted to ammeline and/or ammelide, which then precipitate(s).

The solid-to-solid reaction according to the invention is carried out in an "aqueous reaction mixture" comprising solid substrate and/or product and a biocatalyst in an aqueous phase. Said aqueous phase is a liquid phase in which the predominant solvent is water.

"Biocatalyst" as defined herein is a biological material or moiety derived from a biological source that catalyzes the reaction step(s) in the process according to the invention. The biocatalyst may be in principle any organism, e.g. a microorganism, or a biomolecule derived there from. It may in particular comprise one or more enzymes.

The "amidohydrolase superfamily" is a structure-based cluster of "metal-dependent hydrolase" enzymes which contain a triosephosphate isomerase (TIM)-like barrel fold in the catalytic domain. Members of this superfamily catalyze the cleavage of not only C—N but also C—C, C—O, C—Cl, C—S and O—P bonds of organic compounds (L. Aimin, L. Tingfeng, F. Rong. 2007. Amidohydrolase superfamily. In: Encyclopedia of life sciences 2007).

An "enzyme having aminohydrolase activity towards 1,3,5-triazine compounds" is an enzyme having hydrolytic activity towards amino-substituted 1,3,5-triazine compounds with the ability to convert one or more amino substituents to hydroxy substituents by hydrolysis of the C—N bond between a carbon atom in the triazine ring and the N-atom of the amino substituent, meanwhile generating ammonia (reaction scheme [1]).

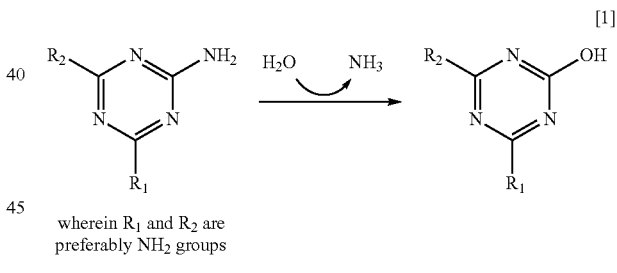

wherein $R_1$ and $R_2$ are preferably $NH_2$ groups

The "enzyme having aminohydrolase activity towards 1,3,5-triazine compounds" is also referred hereafter as "the enzyme".

In comparison with the methods of the prior art, the process according to the invention requires mild conditions. The process is carried out at moderate temperatures in the presence of an aqueous phase for the biocatalyst to remain active. The process is furthermore environment friendly with no use of toxic solvents, halogen-containing compounds or alcohols. The ammeline and/or ammelide directly precipitate(s) in the aqueous reaction mixture and their (its) recovery requires only a few washing steps using water. Another advantage of the process is the production of the desired product without formation of by-products, e.g. cyanuric acid, resulting in a loss of yield. It is envisaged that a method according to the invention allows a better yield than the chemical routes described in the prior art. High maximum conversions of melamine to ammeline and/or ammelide (up to about 99%) are achieved. An additional advantage of the process according to the invention over the chemical routes is the ability to fine-tune the ammeline: ammelide ratio.

The conversion of melamine to ammeline and/or ammelide is said to reach its "maximum conversion" when no significant reaction occurs despite the presence of unreacted substrate and biocatalyst.

Some studies have investigated the contribution of soil bacteria to melamine toxicity in humans and animals and have led to the identification of a bacterial melamine metabolic pathway, in which melamine was shown to be hydrolyzed into ammeline and ammelide by sequential deamination. The genes and enzymes involved in these two deamination steps have been identified and in some cases, the enzymes have been purified and characterized. The latter have been found to belong to the amidohydrolase superfamily (reaction scheme [2]; J. L. Seffernick, A. G. Dodge, M. J. Sadowsky, J. A. Bumpus and L. P. Wackett. 2010. Bacterial ammeline metabolism via guanine deaminase. J. Bacteriology 192(4), 1106-1112; A. G. Dodge, L. P. Wackett, M. J. Sadowsky. 2012. Plasmid localization and organization of melamine degradation genes in Rhodococcus sp. strain Mel. Applied and environmental microbiology 78(5), 1397-1403). These studies do not relate to the technical field of the present invention, i.e. process for the preparation of ammeline and/or ammelide from melamine by a solid-to-solid reaction in an aqueous reaction mixture comprising a biocatalyst, and there has been no indication that the enzymes identified in the bacterial melamine metabolic pathway could be suitably used in the process according to the invention.

The first two steps from the hydrolytic degradation pathway of melamine are shown in reaction scheme [2]. The genes encoding microbial enzymes that catalyze each step are indicated. The triA, trzA, atzB genes are encoding a melamine deaminase, a s-triazine hydrolase and a hydroxyatrazine hydrolase, respectively. GDA is an abbreviation of guanine deaminase. All of the enzymes are members of the amidohydrolase superfamily.

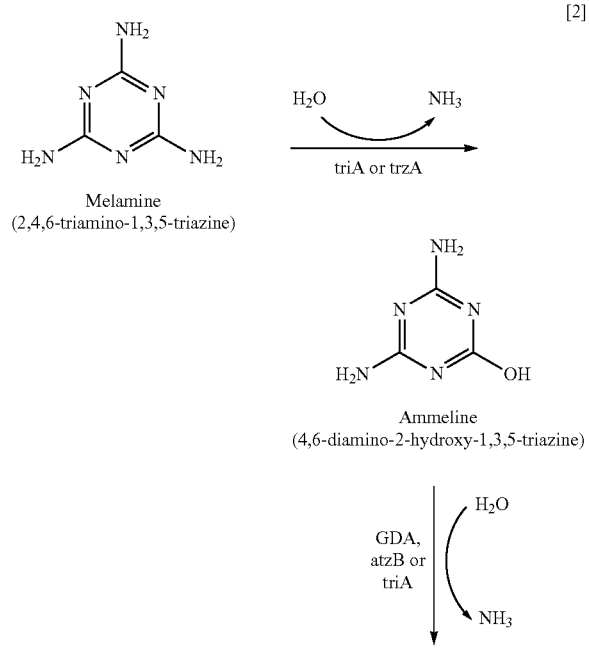

[2]

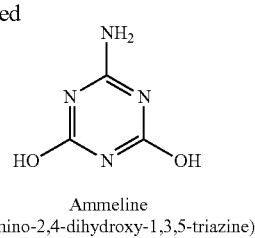

Ammeline
(6-amino-2,4-dihydroxy-1,3,5-triazine)

In accordance with the invention, melamine is converted into ammeline, and optionally ammelide, by a "solid-to-solid" reaction in an aqueous reaction mixture comprising a biocatalyst. Reaction parameters (e.g. biocatalyst, aqueous phase, mixing, pH, temperature or substrate loading) may be varied in order to optimize the reaction and to obtain the desired product.

The biocatalyst according to the invention may be used in any form. The biocatalyst may be used for example in the form of (partially) purified enzyme, lyophilised enzyme powder, immobilized enzyme, whole cells (e.g. permeabilised, freeze-dried), immobilized whole cells, cell lysate or cell free extract.

It will be clear to the skilled person that use can be made of a naturally occurring biocatalyst (wild type) or a mutant of a naturally occurring biocatalyst with suitable activity in the process according to the invention. Properties of a naturally occurring biocatalyst may be improved by biological techniques known to the skilled person, such as e.g. molecular evolution or rational design. Mutants of wild-type biocatalysts can for example be made by modifying the encoding DNA of an organism capable of acting as a biocatalyst or capable of producing a biocatalytic moiety (e.g. an enzyme) using mutagenesis techniques known to the skilled person (e.g. random mutagenesis, site-directed mutagenesis, directed evolution, gene recombination). In particular, the DNA may be modified such that it encodes an enzyme that differs by at least one amino acid from the wild type enzyme, so that it encodes an enzyme that comprises one or more amino acid substitutions, deletions and/or insertions compared to the wild type, or such that the mutants combine sequences of two or more parent enzymes or by effecting the expression of the thus modified DNA in a suitable (host) cell. The latter may be achieved by methods known to the skilled person such as codon pair optimization, e.g. based on a method as described in WO 2008/000632.

A mutant biocatalyst may have improved properties, for instance with respect to one or more of the following aspects: selectivity towards the substrate, activity, stability, solvent tolerance, pH profile, temperature profile, substrate profile, susceptibility to inhibition, cofactor utilisation and substrate-affinity. Mutants with improved properties can be identified by applying e.g. suitable high through-put screening or selection methods based on such methods known to the skilled person.

A cell, in particular a recombinant cell, comprising one or more enzymes for catalysing the reaction step(s) in a process according to the invention can be constructed using molecular biology techniques, which are known in the art per se. For instance, if one or more exogenous enzymes are to be produced in a recombinant cell, such techniques can be used to provide a vector (e.g. a recombinant vector) which comprises one or more exogenous genes encoding one or more of said exogenous enzymes. One or more vectors may be used, each comprising one or more of such exogenous genes. Such vector can comprise one or more regulatory elements, e.g. one or more promoters, which may be operably linked to the gene(s) encoding the enzyme(s).

The term "exogenous" as it is used herein is intended to mean that the biomolecule (e.g. DNA, RNA, protein) is introduced into the host cell. The biomolecule can be, for example, a homologous (or heterologous) nucleic acid that encodes a homologous (or heterologous) protein following introduction into the host cell. The term "heterologous" refers to a biomolecule isolated from a donor source other than the host cell whereas the term "homologous" refers to a biomolecule isolated from the host cell. Accordingly, exogenous expression of an encoding nucleic acid of the invention can utilize either or both heterologous or homologous encoding nucleic acid.

As the inventors have found, the enzyme belonging to the amidohydrolase superfamily and having aminohydrolase activity towards 1,3,5-triazine compounds (as used in the process according to the present invention) can be any suitable enzyme (i.e. the enzyme is suitable if it can be confirmed to have aminohydrolase activity towards 1,3,5-triazine compounds) selected from the group consisting of melamine deaminase (also called melamine amidohydrolase), s-triazine hydrolase (also called N-ethylammeline chlorohydrolase), hydroxyatrazine hydrolase (also called atrazine chlorohydrolase), guanine deaminase (also called guanine amidohydrolase) and simazine chlorohydrolase.

In one embodiment, a suitable melamine deaminase might be selected from the group consisting of melamine deaminases originating from *Acidovorax, Ketogulonicigenium, Pseudomonas, Gordonia, Rhodococcus, Micrococcus, Klebsiella, Williamsia, Nocardia, Arthrobacter, Nesterenkonia, Kocuria, Dermacoccus, Kytococcus* and *Enterobacter*. In particular, said melamine deaminase might originate from *Acidovorax citrulii* (formerly called *Pseudomonas citrulii*), *Acidovorax avenae* subspecies *citrulii* (formerly called *Pseudomonas pseudoalcaligenes* subsp. *citrulii*), *Ketogulonicigenium vulgare, Gordonia rubripertinctus* (also called *Gordona rubripertincta*; synonym to *Rhodococcus coraffinus*), *Klebsiella terragena* or *Micrococcus* sp. strain MF-1. More particularly, said melamine deaminase might originate from *Acidovorax citrulii* NRRL B-12227 or *Ketogulonicigenium vulgare* Y25.

In another embodiment, a suitable s-triazine hydrolase may be selected from the group consisting of s-triazine hydrolases originating from *Gordonia, Rhodococcus, Saccharopolyspora, Streptococcus, Streptomyces, Enterococcus, Abiotrophia, Lactococcus, Ruminococcus, Gemalla, Atopobium, Streptoverticifiium, Actinoplanes, Kitasatospora, Chainia* and *Actinosporangium*. A suitable s-triazine hydrolase may in particular be selected from *Gordonia rubripertinctus* (also called *Gordona rubripertincta*; synonym to *Rhodococcus coraffinus*), more particularly from *Rhodococcus coraffinus* NRRL B-15444R.

In a further embodiment, a suitable hydroxyatrazine hydrolase may originate from *Arthrobacter, Beta* proteobacterium, *Pseudomonas, Aminobacter, Micrococcus, Aureobacterium, Corynebacterium, Rhodococcus, Brevibacterium, Nocardioides, Terrabacter, Comamonas, Burkholderia, Brevundimonas, Vogesella, deleya, Methylobacterium, Herbaspirillum, Hydrogenophaga* or *Pseudoalteromonas*. In particular, a suitable hydroxyatrazine hydrolase may originate from *Pseudomonas* sp. ADP or *Aminobacter aminovorans*.

In yet a further embodiment, a suitable guanine deaminase may be selected from the group consisting of guanine deaminases originating from *Bradyrhizobium, Escherichia, Rhizobium* and *Leclercia*. In particular, said guanine deaminase may originate from *Bradyrhizobium japonicum* or *Escherichia coli*. More particularly, said guanine deaminase may originate from *Bradyrhizobium japonicum* USDA 110 or *Escherichia coli* ETEC H10407.

In yet a further embodiment, a suitable simazine chlorohydrolase may be selected from the group consisting of simazine chlorohydrolases originating from *Herbaspirillum*. In particular, said simazine chlorohydrolase may originate from *Herbaspirillum* sp. B601.

In a specific embodiment, the enzyme belonging to the amidohydrolase superfamily and having aminohydrolase activity towards 1,3,5-triazine compounds comprises an amino acid sequence represented by SEQ ID NO: 5 (AAG41202.1), SEQ ID NO: 6 (YP_003963954.1), SEQ ID NO: 7 (Q52725.2), SEQ ID NO: 8 (NP_770520.1) and SEQ ID NO: 9 (CBJ02579.1) or a homologue thereof.

A "homologue" is used herein in particular for a polypeptide having a sequence identity of at least 30% with its reference protein (i.e. SEQ ID NO: 5, 6, 7, 8 or 9), preferably at least 40%, more preferably at least 50%, more preferably at least 60%, more preferably at least 65%, more preferably at least 70%, more preferably at least 75%, more preferably at least 80%, in particular at least 85%, more in particular at least 90%, at least 91%, at least 92%, at least 93%, at least 94%, at least 95%, at least 96%, at least 97%, at least 98% or at least 99%. A homologue is generally a polypeptide that has functional and, preferably, also structural similarity to its reference protein. One type of homologue is encoded by a gene from another species of the same genus or even from other genera. "Homologue" is also intended to include those proteins which have been altered by mutagenesis techniques that have been performed to improve the protein's desired properties.

Sequence identity is herein defined as a relationship between two or more polypeptide sequences or two or more nucleic acid sequences, as determined by comparing the sequences. Usually, sequence identities are compared over the whole length of the sequences, but may however also be compared only for a part of the sequences aligning with each other. In the art, "identity" also means the degree of sequence relatedness between polypeptide sequences or nucleic acid sequences, as the case may be, as determined by the match between such sequences. Preferred methods to determine identity are designed to give the largest match between the sequences tested. In the context of this invention a preferred computer program method to determine identity between two sequences includes BLASTP and BLASTN (Altschul, S. F. et al., J. Mol. Biol. 1990, 215, 403-410, publicly available from NCBI and other sources (BLAST Manual, Altschul, S., et al., NCBI NLM NIH Bethesda, Md. 20894). Preferred parameters for polypeptide sequence comparison using BLASTP are gap open 10.0, gap extend 0.5, Blosum 62 matrix. Preferred parameters for nucleic acid sequence comparison using BLASTN are gap open 10.0, gap extend 0.5, DNA full matrix (DNA identity matrix).

The aqueous phase in the process of the invention is a liquid phase in which the predominant solvent is water. The aqueous phase might be water only, a buffer comprising a mixture of water and a buffering salt/buffering salts (e.g. potassium phosphate buffer), a mixture of water with an organic solvent (e.g. ethylene glycol, DMSO (dimethyl sulfoxide), THF (tetrahydrofuran)) or mixture of buffer with an organic solvent (e.g. ethylene glycol, DMSO, THF). A skilled person will be able to select and optimize the aqueous phase for efficient activity of the biocatalyst.

Due to the nature of the solid-to-solid reaction, effective mixing of the aqueous reaction mixture is important to provide good transport and contact of the reaction components and to avoid particle settling. A skilled person will be able to select the right mixer design and mixing conditions using commercially available techniques. Efficient mixing can for instance be done by a radial pumping stirrer, while particle settling can be avoided by an axial stirrer, pumping downward to the bottom of the reaction vessel. As axial pumping impellers narrow blade hydrofoils are used as state-of-the-art. Traditionally pitched bladed turbines as standard impellers are used. Propellers can be used in an off centered position as well. When using centered impellers, baffling can be applied to turn the flow swirling to the desired pattern of the impeller. Providing mixing by pumping the aqueous reaction mixture via an outer loop is also an option. It was surprisingly found that the enzymes used in the process according to the invention survive the hydrodynamic shear forces which arise due to the mixing and the presence of undissolved solids.

In principle, the pH of the reaction medium may be chosen within wide limits, as long as the biocatalyst is active under the pH conditions applied. The pH of the reaction mixture is suitably between 4 and 11, preferably between 5 to 10. A pH selected between A and B, a pH ranging from A to B or a pH range of A to B comprises the end points A and B.

The inventors have surprisingly found that the pH has a profound effect on the ammeline:ammelide ratio. Example 2 and Table 3 illustrate this effect. Under the conditions applied and within a pH range of 7 to 10, a higher pH resulted in a higher ammeline:ammelide ratio. In particular, pH of 7, 8, 9, 9.5 and 10 resulted in ammeline:ammelide ratios of 3.5 (75.2 mol % ammeline, 21.2 mol % ammelide), 14.3 (90.0 mol % ammeline, 6.3 mol % ammelide), 56.8 (96.5 mol % ammeline, 1.7 mol % ammelide), 108.8 (97.9 mol % ammeline, 0.9 mol % ammelide) and 164 (98.4 mol % ammeline, 0.6 mol % ammelide), respectively. An inverse trend was observed at pH values below 7, wherein a higher pH resulted in a lower ammeline:ammelide ratio. In particular, the ammeline:ammelide ratios were of 18.3 (91.5 mol % ammeline, 5.0 mol % ammelide) and 8.8 (86.9 mol % ammeline, 9.9 mol % ammelide) at a pH of 5 and 6, respectively. In other words, under the conditions applied and within a pH ranging from 6.5 and 7.5, a product with high ammelide content was obtained, whereas at pH below 6.5, preferably below 6 or at pH above 7.5, preferably above 8, a product with high ammeline content was formed. The pH has therefore been identified as an important parameter for fine-tuning the ammeline:ammelide ratio.

In principle, the temperature of the reaction medium used may be chosen within wide limits, as long as the biocatalyst remains active under the temperature conditions applied. In the process according to the invention, the reaction temperature is normally between 0 and 100° C., preferably between 10 and 60° C.

In the process according to the invention, the melamine substrate is added to the aqueous reaction mixture at loadings above saturation to form a solid within the temperature and pH ranges to be selected in the invention. Melamine loadings at which melamine forms a solid at a selected reaction condition can be determined by routine experiments.

As meant herein, the term "loading" is the total mass of melamine initially added to the reaction mixture, relative to the total mass of the aqueous reaction mixture. The melamine loading is expressed as mass percentage (mass %).

"Saturation" is defined herein as a point of maximum loading at which a solution of melamine can no more dissolve any additional amounts of melamine and such additional amounts of melamine will appear as a solid.

In one embodiment of the invention, melamine is present in a loading of at least 1.0 mass %, relative to the total mass of the aqueous reaction mixture, preferably at least 10 mass %, more preferably at least 15 mass %, still more preferably at least 20 mass %, even more preferably at least 30 mass %

The inventors have surprisingly found that the substrate loading has a profound effect on the composition of the final product, wherein a higher melamine loading results in a higher ammeline:ammelide ratio. Example 3 and Table 4 illustrate this effect. Under the conditions applied, initial melamine loadings of about 1 mass %, 9 mass % and 17.5 mass % resulted in ammeline:ammelide ratios of 108.8 (97.9 mol % ammeline, 0.9 mol % ammelide), 329.7 (98.9 mol % ammeline, 0.3 mol % ammelide), 494 (98.8 mol % ammeline, 0.2 mol % ammelide), respectively. Melamine loading has therefore been identified as another important parameter for fine-tuning the ammeline:ammelide ratio.

After the solid-to-solid reaction has proceeded to an acceptable conversion level, the solid product can be isolated from the aqueous reaction mixture by conventional methods (e.g. by filtration, by centrifugation or by applying a decanter centrifuge). Subsequently, the isolated product can be washed with water for removal of residual melamine substrate. The ammeline:ammelide ratio is not affected by these washing steps.

The solid product obtainable by the process according to the invention has high ammeline and/or ammelide content and low level of residual melamine. Suitably the product comprises at least 95 mass % of ammeline and/or ammelide and at most 5 mass % of melamine. Preferably, the product comprises at least 98 mass % of ammeline and/or ammelide and at most 2 mass % of melamine. More preferably, the product comprises at least 99 mass % of ammeline and/or ammelide and at most 1 mass % of melamine.

In principle, the ammeline:ammelide ratio of the solid product can be fine-tuned within a wide range. Typically, ammeline is in excess of ammelide. Suitably, the solid product has an ammeline:ammelide ratio in the range of 1-1000, more suitably in the range of 2-500.

The invention further relates to all possible combinations of different embodiments and/or preferred features according to the process of the invention as described herein.

The invention is elucidated with reference to the following examples, without however being restricted by these.

EXAMPLES

Materials and General Methods
1. Melamine Substrate; Reference Materials Ammeline, Ammelide and Cyanuric Acid Melamine (from OCl-Nitrogen), with a chemical purity of >99.9% was applied for the examples.

Ammeline (from Hicol) with a chemical purity of 97.5% was used as reference material in HPLC analyses.

Ammelide with a chemical purity of 99.7% was used as reference material in HPLC analyses.

Cyanuric acid with a chemical purity of >99% was used as reference material in HPLC analyses.

2. Preparation of Biocatalysts

2.a. Cloning and Expression of Recombinant Enzymes

Five genes from different organisms encoding enzymes with aminohydrolase activity towards 1,3,5-triazine compounds were selected to exemplify the invention; namely SEQ ID NO: 10 (gi_11890745), SEQ ID NO: 11 (gi_310815990), SEQ ID NO: 12 (gi_4033703), SEQ ID NO: 13 (gi_27378991) and SEQ ID NO: 14 (gi_309703244) encoding SEQ ID NO: 5 (AAG41202.1), SEQ ID NO: 6 (YP_003963954.1), SEQ ID NO: 7 (Q52725.2), SEQ ID NO: 8 (NP_770520.1) and SEQ ID NO: 9 (CBJ02579.1), respectively (Table 1).

TABLE 1

Overview of enzymes, donor organisms, accession numbers and recombinant vectors.

| Enzyme | Enzyme SEQ ID NO (accession number) | Gene SEQ ID NO (accession number) | Codon pair optimized gene[*] SEQ ID NO | Recombinant vectors |
|---|---|---|---|---|
| Melamine deaminase from *Acidovorax citrulli* NRRL B-12227 | 5 (AAG41202.1) | 10 (gi_11890745) | 1 | pBAD_Meldeam_Aci |
| Melamine deaminase from *Ketogulonicigenium vulgare* Y25 | 6 (YP_003963954.1) | 11 (gi_310815990) | 2 | pBAD_Meldeam_Kvu |
| s-Triazine hydrolase from *Rhodococcus corallinus* NRRL B-15444R | 7 (Q52725.2) | 12 (gi_4033703) | 3 | pBAD_TrzA_Rco |
| Guanine deaminase from *Bradyrhizobium japonicum* USDA 110 | 8 (NP_770520.1) | 13 (gi_27378991) | 4 | pBAD_Guadeam_Bja |
| Guanine deaminase from *Escherichia coli* ETEC H10407 | 9 (CBJ02579.1) | 14 (gi_309703244) | — | pBAD_Guadeam_Eco |

[*] For expression in *Escherichia coli*

Four out of the five target genes, i.e. SEQ ID NO: 10, SEQ ID NO: 11, SEQ ID NO: 12 and SEQ ID NO: 13, were codon pair optimized for expression in *Escherichia coli*, resulting in SEQ ID NO: 1, SEQ ID NO: 2, SEQ ID NO: 3 and SEQ ID NO: 4, respectively (sequence listing). Codon pair optimization was performed according to a procedure described in WO2008/000632.

For larger scale expression experiments, *E. coli* RV311 cells were made chemically competent using the Z-Competent™ *E. coli* Transformation Kit (Zymo Research, Irvine, Calif., USA) and transformed with the pBAD recombinant vectors isolated as described above from the *E. coli* TOP10 strains. Transformants were selected on LB agar plates containing 100 μg/ml neomycin. From these plates 50 ml precultures in LB medium containing 50 μg/ml neomycin were inoculated and incubated on an orbital shaker at 180 rpm and 28° C. After overnight incubation the precultures were used to inoculate 1 l LB expression cultures (in 2 l baffled Erlenmeyer flasks) to starting $OD_{620}$s of 0.05. These expression cultures were incubated on an orbital shaker at 180 rpm and 28° C. In one third of the cultures, the melamine deaminase gene expression was induced after 8 h by addition of 0.02% (w/v) L-arabinose and incubation was continued overnight. Subsequently these cultures were harvested by centrifugation at 10,000 g for 10 min. The other two third of the cultures were also incubated overnight and induced as described above after approximately 24 h. After 4 and 8 h, respectively, also these cultures were harvested by centrifugation.

2.b. Fermentation of Biocatalyst on 10 l Scale

Fermentation of *E. coli* RV311 expressing the pBAD recombinant vectors was performed in a fed-batch fermentation on 10 l scale, using glucose as a carbon source.

2.c. Preparation of Cell Free Extract on Small Scale (1-10 ml)

The cell pellets were resuspended in twice the volume of their wet weight with ice-cold 100 mM potassium phosphate buffer pH 7.0. Cell-free extracts (CFEs) were obtained by sonification of the cell suspensions using a Sonics (Meyrin/Satigny, Switzerland) Vibra-Cell VCX130 sonifier (output 100%, 10 sec. on/10 sec. off, for 10 min) with cooling in an ice/acetone bath and subsequent centrifugation in an Eppendorf 5415R centrifuge (Hamburg, Germany) at 13,000×g and 4° C. for 30 min. The supernatants (=CFEs) were transferred to fresh tubes and stored on ice for immediate use or stored at −20° C.

2.d. Preparation of Cell Free Extract on Larger Scale (10-250 ml Scale)

To 76.3 g wet cells (frozen), 152.6 g potassium phosphate buffer (100 mM pH=7) was added. Cells were suspended and put on ice. Subsequently, 1125 mg lysozym and 50 μl benzonase were added, mixed and put at −20° C. overnight. The next morning the suspension was put at 37° C. room on a shaker for 2.25 h. The suspension was cooled afterwards on ice and subsequently divided over 8 tubes of 50 ml (~28 ml each) and each suspension was sonicated for 2 min, using a Sonics (Meyrin/Satigny, Switzerland) Vibra-Cell VCX130 sonifier (output 100%, 10 sec. on/10 sec. off, for 10 min) with cooling in an ice/acetone bath. Subsequently, the suspensions were stored on ice at 4° C. room for 4 h. Next, the suspensions were centrifuged at 15.000 rpm for 15 min. The obtained supernatants were collected and stored at −20° C.

3. Protein Determination

The protein concentrations in the CFEs were determined using a modified protein-dye binding method as described by Bradford in Anal. Biochem. 72: 248-254 (1976). Of each sample 50 µl in an appropriate dilution was incubated with 950 µl reagent (100 mg Brilliant Blue G250 dissolved in 46 ml ethanol and 100 ml 85% ortho-phosphoric acid, filled up to 1,000 ml with Milli-Q water) for at least five minutes at room temperature. The absorption of each sample at a wavelength of 595 nm was measured in a PerkinElmer Lambda35 UV/VIS spectrophotometer. Using a calibration line determined with solutions containing known concentrations of bovine serum albumin (BSA, ranging from 0.0125 mg/ml to 0.20 mg/ml), the protein concentration in the samples was calculated.

4. SDS-PAGE Analysis

The recombinant expression in *E. coli* was analyzed by SDS-PAGE of the *E. coli* TOP10 CFEs and of the *E. coli* RV 311 CFEs and compared to a CFE with an overexpressed control protein.

5. Conversion Reactions and Product Isolation 5.a. Conversion Reactions—General Description Conversion reactions were either performed in a glass reactor of 80 ml containing a propeller stirrer or in a glass reactor of 1600 ml, containing a turbine stirrer and pH-stat equipment (type 718 Stat Titrino from Metrohm). A stirrer speed of about 500 rpm was applied.

In general, a conversion was performed as follows: a certain amount of melamine was added to a buffer (100 mM $K_2HPO_4$/1 mM $MgSO_4.7H_2O$) at 37° C. to reach a desired loading. The pH was adjusted to the desired value, using 1M $H_3PO_4$ (for obtaining a pH of 7 or lower) or 1M NaOH (for obtaining a pH of 8 or higher). Subsequently, the biocatalyst was added to start the conversion. Samples were taken in the course of the conversion for HPLC analysis as described in paragraph 6.

5.b. Product Isolation

Product isolation was performed after a certain reaction time by pouring the reaction mixture over a P3 glass filter, using vacuum (about 750 mbar). The filter cake was washed three times with water. The obtained product was dried overnight.

6. HPLC Analysis 6.a. Sample Preparation for HPLC-Analysis

Samples of the aqueous reaction mixtures or samples of the isolated products were diluted in first instance with formic acid to a total 1,3,5-triazine compounds concentration of about 0.5 mass % and subsequently diluted 50 times with water before subjecting to HPLC analysis.

6.b. HPLC Analysis Method

Two 250 mm Prevail C18 columns are used. The critical separation takes place at 0% acetonitrile. The columns are to be equilibrated for at least 8 minutes after the gradient. The specific analytical conditions on the HPLC used are:
Columns: Prevail C18 2× (250 mm×4.6 mm ID×5 □m)
Eluent A: $HClO_4$ pH=2.0 (1.63 g 70% $HClO_4$/l water)
Eluent B: Acetonitrile
Flow: 1.2 ml/min
Injection volume: 5 µl
Column temperature: 15° C.
Detection wavelength: 195 nm

| Time (min) | % B |
|---|---|
| 0 | 0 |
| 12 | 0 |
| 12.5 | 80 |
| 13.5 | 80 |
| 14 | 0 |
| 22 | Stop |

Example 1: Preparation of Ammeline and/or Ammelide from Melamine by a Solid-to-Solid Reaction in an Aqueous Reaction Mixture Reactions were performed in 80 ml reactors with a filling volume of about 55 ml, containing a stirrer and pH-stat equipment.

For the test reaction, 555 mg of melamine was added to 47 g buffer (100 mM $K_2HPO_4$/1 mM $MgSO_4.7H_2O$) at 37° C. The pH was adjusted to pH 9.5 with 1.65 g 1M NaOH. Subsequently, 0.25 ml of cell free extract of *E. coli* RV311 pBAD_Meldeam_Aci was added to start the reaction, thereby obtaining a final concentration of cell free extract of 0.5 vol %. The melamine loading was 1.1 mass %. The pH was kept constant at 9.5 by titration with 1 M NaOH.

A chemical blank reaction was run in parallel, using the same procedure as described above, with the exception that no biocatalyst was added. A biological blank reaction was run in parallel, using the same procedure as described above, with the exception that cell free extract is obtained from *E. coli* RV311 harboring a pBAD recombinant vector having a gene insert that encodes an enzyme not able to convert melamine (in this case a P450 monooxygenase enzyme from *Bacillus megaterium* BM3).

After 18 h reaction time, samples were taken from the three reaction mixtures for HPLC analysis. Results are shown in Table 2.

TABLE 2

HPLC analyses of the reaction mixtures after 18 h reaction time

| Reaction mixture | Melamine (mol %) | Ammeline (mol %) | Ammelide (mol %) | Cyanuric acid (mol %) | Conversion (%) |
|---|---|---|---|---|---|
| Test reaction | 1.2 | 97.7 | 1.1 | 0 | 98.8 |
| Chemical blank | 99.8 | 0.2 | 0.0 | 0 | 0.2 |
| Biological blank | 99.9 | 0.1 | 0.0 | 0 | 0.1 |

The results in Table 2 show that the conversion of melamine to ammeline and ammelide is due to the activity of the biocatalyst (i.e. cell free extract of *E. coli* RV311 pBAD_Meldeam_Aci). The melamine initially added to the reaction mixture is almost fully converted to ammeline and ammelide within 18 h. No cyanuric acid was formed. No significant conversion of melamine took place in the chemical blank reaction mixture, showing that the melamine is chemically stable during the reaction time, under the conditions applied. Furthermore, no significant conversion of melamine took place in the biological blank reaction mixture.

Example 2: Effect of pH on the Ammeline:Ammelide Ratio

Conversion reactions were performed in 80 ml reactors with a filling volume of about 55 ml containing a stirrer and pH-stat equipment.

555 mg of melamine was added to 47 g buffer (100 mM K$_2$HPO$_4$/1 mM MgSO$_4$.7H$_2$O) at 37° C. The pH was adjusted to the desired value, using 1M H$_3$PO$_4$ (for obtaining a pH of 7 or lower) or 1M NaOH (for obtaining a pH of 8 or higher). Subsequently, 0.25 ml of cell free extract of *E. coli* RV311 pBAD_Meldeam_Aci was added to start the reaction, thereby obtaining a final concentration of cell free extract of 0.5 vol %. The melamine loading was 1.1 mass %. The pH was kept constant by titration with 1 M H$_3$PO$_4$ or 1 M NaOH. Samples were taken over time for HPLC analysis. At maximum conversion, the solid products were isolated and analyzed as described in "materials and general methods". Results are shown in Table 3.

TABLE 3

Maximum conversion and analysis results of the isolated solid products

| pH | Melamine (mass %) | Ammeline (mass %) | Ammelide (mass %) | Ammeline:ammelide ratio at maximum conversion | Conversion (%) |
| --- | --- | --- | --- | --- | --- |
| 5 | 3.5 | 91.5 | 5.0 | 18.3 | 96.1 |
| 6 | 3.2 | 86.9 | 9.9 | 8.8 | 96.8 |
| 7 | 3.6 | 75.2 | 21.2 | 3.5 | 96.4 |
| 8 | 3.7 | 90.0 | 6.3 | 14.3 | 96.3 |
| 9 | 1.8 | 96.5 | 1.7 | 56.8 | 98.2 |
| 9.5 | 1.2 | 97.9 | 0.9 | 108.8 | 98.8 |
| 10 | 1.0 | 98.4 | 0.6 | 164 | 99.0 |

The results in Table 3 show that the ammeline:ammelide ratio obtained in the reaction mixture can be fine-tuned by the pH. Within a pH range of 7 to 10, the higher the pH, the higher the ammeline:ammelide ratio. An inverse trend was observed at pH values below 7, wherein a higher pH resulted in a lower ammeline:ammelide ratio. It is noteworthy to mention that cyanuric acid was never detected.

Example 3: Effect of Melamine Loading on the Ammeline:Ammelide Ratio

Conversion reactions were performed in 80 ml reactors with a filling volume of about 55 ml containing a stirrer and pH-stat equipment.

Melamine was added to 47 g buffer (100 mM K$_2$HPO$_4$/1 mM MgSO$_4$.7H$_2$O) at 37° C. to a loading of 1.1 mass %, 9 mass % or 17.5 mass %. The pH was adjusted to 9.5 using 1 M NaOH. Subsequently, to start the reactions, cell free extract of *E. coli* RV311 pBAD_Meldeam_Aci was added to a concentration of 0.5 vol %, 5 vol % or 10 vol %, respectively. The pH was kept constant during the conversion by titration with 1 M NaOH. Samples were taken over time for HPLC analysis. At maximum conversion, the solid products were isolated and analyzed as described in "materials and general methods". Results are shown in Table 4.

The results in Table 4 show that at the chosen reaction conditions, the ammeline:ammeline ratio can be fine-tuned by adjusting the melamine loading; the higher the melamine loading under the chosen reaction conditions, the higher the ammeline:ammelide ratio. It is noteworthy to mention that cyanuric acid was never detected.

Example 4: Preparation of Ammeline and/or Ammelide by a Solid-to-Solid Reaction in an Aqueous Mixture on 1 l Scale A reaction mixture was prepared in a stirred 1.6 l glass reactor, by adding 125.2 g melamine to 1050 ml buffer (100 mM K$_2$HPO$_4$/1 mM MgSO$_4$.7H$_2$O). The melamine solid substrate was stirred for 20 min at 37° C. after which the pH was adjusted to pH 9.5 by adding 0.05 g 5M NaOH. To start the reaction 62.5 ml of cell free extract of *E. coli* RV311 pBAD_Meldeam_Aci was added (5 vol %), after which the pH was adjusted to pH 9.5 by adding another 0.1 g of 5 M NaOH. The melamine loading was 10.1 mass %. During the conversion, the pH was kept constant at pH 9.5 by titrating a solution of 1M H$_3$PO$_4$ applying a pH-stat equipment. Samples were taken for HPLC analysis. After 5 h, the reaction was stopped and the solid product was isolated and analyzed as described in "materials and general methods". A total of 125 g of product was obtained, containing 98.6 mass % ammeline, 0.4 mass % ammelide and 1 mass % melamine, corresponding to a conversion of 99%. No cyanuric acid was formed.

TABLE 4

Maximum conversion and analysis results of the isolated solid products

| Melamine loading (mass %) | Melamine (mass %) | Ammeline (mass %) | Ammelide (mass %) | Ammeline:ammelide ratio at maximum conversion | Conversion (%) |
| --- | --- | --- | --- | --- | --- |
| 1.1 | 1.2 | 97.9 | 0.9 | 108.8 | 98.8 |
| 9 | 0.8 | 98.9 | 0.3 | 329.7 | 99.2 |
| 17.5 | 1.0 | 98.8 | 0.2 | 494.0 | 99.0 |

The invention claimed is:

1. A process for the preparation of ammeline and optionally ammelide from melamine comprising:
   a) contacting solid melamine in an aqueous reaction mixture with a biocatalyst;
   b) incubating the aqueous reaction mixture comprising solid melamine and the biocatalyst for sufficient time to convert the melamine into a product comprising solid ammeline: and
   c) recovering the product, wherein the biocatalyst comprises at least one enzyme belonging to the amidohydrolase superfamily and having amidohydrolase activity towards 1, 3, 5-triazine compounds, and wherein the at least one enzyme comprises an amino acid sequence having at least 90% sequence identity to the sequence selected from the group consisting of SEQ ID NO: 5, SEQ ID NO: 6, SEQ ID NO: 7, SEQ ID NO: 8 and SEQ ID NO: 9.

2. The process according to claim 1, wherein the enzyme comprises an amino acid sequence selected from the group consisting of SEQ ID NO: 5, SEQ ID NO: 6, SEQ ID NO: 7, SEQ ID NO: 8 and SEQ ID NO: 9.

3. The process according to claim 1, wherein the melamine is present in a loading of at least 1.0 mass %, relative to the total mass of the aqueous reaction mixture before the contacting with the biocatalyst.

4. The process according to claim 3, wherein the melamine is present in a loading of at least 10 mass %, relative to the total mass of the aqueous reaction mixture.

5. The process according to claim 4, wherein the melamine is present in a loading of at least 20 mass %, relative to the total mass of the aqueous reaction mixture.

6. The process according to claim 1, wherein the melamine is converted into ammeline, and optionally ammelide, at a pH selected between 5 and 10.

7. The process according to claim 6, wherein the melamine is converted into ammeline, and optionally ammelide, at a pH selected between 6.5 and 7.5.

8. The process according to claim 6, wherein the melamine is converted into ammeline, and optionally ammelide, at a pH selected below 6.5.

9. The process according to claim 6, wherein the melamine is converted into ammeline, and optionally ammelide, at a pH selected above 7.5.

10. The process according to claim 1, wherein the aqueous reaction mixture comprises an organic solvent.

11. The process according to claim 1, wherein at least about 96% of the melamine is converted into ammeline and ammelide.

12. The process according to claim 1, wherein the process produces substantially no cyanuric acid.

13. The process according to claim 1, wherein the product comprises at least 95 mass % of ammeline and ammelide and no more than 5 mass % of melamine.

* * * * *

SEQUENCE LISTING

<160> NUMBER OF SEQ ID NOS: 14

<210> SEQ ID NO 1
<211> LENGTH: 1422
<212> TYPE: DNA
<213> ORGANISM: Artificial Sequence
<220> FEATURE:
<221> NAME/KEY: source
<222> LOCATION: 1..1422
<223> OTHER INFORMATION: /organism="Artificial Sequence"
    /note="Codon pair optimized Acidovorax citrulli NRRL B-12227
    melamine deaminase gene for E. coli"
    /mol_type="unassigned DNA"

<400> SEQUENCE: 1
atgcagactc tgtctatcca gcacggtact ctggttacca tggaccagta ccgtcgcgta 60
ctgggtgact cctgggttca cgttcaggac ggtcgtatcg ttgcgctggg tgttcacgct 120
gaatccgtac cgccgccagc tgaccgcgtt atcgacgcac gtggtaaagt tgttctgccg 180
ggcttcatca acgcacacac tcacgttaac cagatcctgc tgcgcggtgg tccgtctcac 240
ggtcgtcagc tgtacgactg gctgttcaac gttctgtacc cgggtcagaa agcgatgcgt 300
ccggaagacg ttgctgttgc tgtacgtctg tactgcgcag aagcggtacg ttctggtatc 360
accactatca acgacaacgc tgactccgct atctacccgg gtaacatcga agctgcaatg 420
gcggtttacg gtgaagttgg cgtacgcgtt gtttacgcac gtatgttctt cgaccgtatg 480
gacggtcgta ttcagggtta cgttgatgca ctgaaagcgc gttctccgca ggttgaactg 540
tgctccatca tggaagaaac tgctgttgct aaagaccgta tcactgcgct gtctgaccag 600
taccacggta ctgctggcgg tcgtatctcc gtatggccgg caccggcaat cactccggca 660
gtaactgttg aaggtatgcg ctgggcgcag gcattcgctc gcgaccgtgc ggtaatgtgg 720
actctgcaca tggctgaatc tgaccacgac gaacgtctgc actggatgtc tccggcagaa 780
tacatggagt gctacggtct gctggatgag cgtctgcagg ttgctcactg cgtttacttc 840
gaccgtaaag acgttcgtct gctgcaccgt cacaacgtta aagttgcttc tcaggttgtt 900
tctaacgctt acctgggttc tggtgttgct ccggtaccgg aaatggttga gcgtggtatg 960
gctgttggta tcggtactga cgacggtaac tgcaacgact ccgttaacat gatcggtgac 1020
atgaagttca tggcgcacat ccaccgcgct gttcaccgcg acgctgacgt tctgactccg 1080
gaaaaaatcc tggaaatggc gactatcgac ggtgcgcgtt ctctgggtat ggaccacgaa 1140
atcggttcta tcgaaaccgg taagcgcgct gacctgattc tgctggatct gcgtcacccg 1200
cagactactc cgcaccacca cctggctgca actatcgttt tccaggctta cggtaacgaa 1260
gttgataccg ttctgatcga cggtaacgtt gtaatggaaa accgtcgtct gtctttcctg 1320
ccgccagaac gtgaactggc attcctggaa gaagcgcagt ctcgcgcaac tgctatcctg 1380
cagcgtgcta acatggttgc taacccggca tggcgttccc tt 1422

<210> SEQ ID NO 2
<211> LENGTH: 327
<212> TYPE: DNA
<213> ORGANISM: Artificial Sequence
<220> FEATURE:
<221> NAME/KEY: source
<222> LOCATION: 1..327
<223> OTHER INFORMATION: /organism="Artificial Sequence"
/note="Codon pair optimized Ketogulonicigenium vulgare Y25
melamine deaminase gene for E. coli"
/mol_type="unassigned DNA"

<400> SEQUENCE: 2

```
atgcgtgaag ttctggagtt cgcaactatc aacggtgcga aaggtctgcg tctggatcac    60
aaaaccggtt ctctgactcc gggtaaagaa gctgacatca tcctgctgga cgcaactgcg   120
ctgaacgttg ctccgctgaa caacgcaccg ggtgctgttg ttactctgat ggaacgttct   180
aacgttgaaa ccgtactggt tgctggtcag atcaagaagt ggcagggtgc gctgatcggt   240
caggacatcg ctgcactgcg tgaccagatc atcgcttctc gcgactacct gttcgaagct   300
gctggcgtag aagttccgct gttcgac                                       327
```

```
<210> SEQ ID NO 3
<211> LENGTH: 1431
<212> TYPE: DNA
<213> ORGANISM: Artificial Sequence
<220> FEATURE:
<221> NAME/KEY: source
<222> LOCATION: 1..1431
<223> OTHER INFORMATION: /organism="Artificial Sequence"
      /note="Codon pair optimized Rhodococcus corallinus NRRL B-15444R
      triazine hydrolase gene for E. coli"
      /mol_type="unassigned DNA"

<400> SEQUENCE: 3
```

```
atgactcgta tcgctatcac tggcggtcgc gtactgacca tggacccgga acgtcgcgtt    60
ctggaaccgg gtactgttgt tgttgaagat cagttcatcg ctcaggttgg ttctccgact   120
acttctactt ctgctgcacc gaaatcttcc actccgccag ctggcagtg ctctccggct    180 tcttccactc cgactccgac ttctcacaaa tcttcttccg tgttgttca cccgatgact    240 gcaacttctt ctaacggttg caccacttgc tccatcccgg catctctgcc gactcagact   300
accacttctg aatctgaaca ctgctgcact gcaccgaagc cgttcgttct ggcttctccg   360
ctgtcttcca ccactcgtac ttctgacccg actacttctc cggcaccagg tccgccaggt   420
tctccgttca ctgacgcagg tatccgtgct atctacgcac gtatgtactt cgacgcaccg   480
cgcgctgaac tggaagagct ggttgcaact atccacgcga aagcgccggg tgcggtacgt   540
atggacgaat ctgcttctac tgaccacgta ctggctgacc tggatcagct gatcactcgt   600
cacgaccgta ctgctgacgg tcgtatccgc gtatggccgg caccggcaat cccgttcatg   660
gtttctgaaa aaggtatgaa agcggcacag gaaatcgctg cttcccgtac tgacggctgg   720
accatgcacg tttctgaaga tccgatcgaa gcgcgcgttc actctatgaa cgcaccggaa   780
tacctgcacc acctgggttg cctggatgac cgtctgctgg cagctcactg cgtacacatc   840
gactcccgcg atatccgtct gttccgtcag cacgacgtta agatctccac tcagccggtt   900
tctaactctt acctggctgc tggtatcgct ccggttccgg aaatgctggc gcacggtgtt   960
accgttggta tcggtactga cgacgctaac tgcaacgact ccgttaacct gatttctgac  1020
atgaaagttc tggcgctgat ccaccgcgct gctcaccgcg acgcttctat catcactccg  1080
gaaaaaatca tcgaaatggc gactatcgac ggtgcgcgtt gcatcggtat ggctgaccag  1140
atcggttctc tggaagcagg taagcgcgct gacatcatca ctctggatct gcgtcacgct  1200
cagactactc cggcacacga cctggcggca actatcgttt tccaggctta cggtaacgaa  1260
gttaacgacg ttctggttaa cggttctgtt gtaatgcgtg accgcgttct gtctttcctg  1320
ccgactccgc aggaagagaa agcgctgtac gacgacgctt ctgaacgttc tgctgcgatg  1380
ctggcgcgtg ctggtctgac cggtactcgt acctggcaga ctctgggcag c           1431
```

```
<210> SEQ ID NO 4
<211> LENGTH: 1395
```

<212> TYPE: DNA
<213> ORGANISM: Artificial Sequence
<220> FEATURE:
<221> NAME/KEY: source
<222> LOCATION: 1..1395
<223> OTHER INFORMATION: /organism="Artificial Sequence"
       /note="Codon pair optimized Bradyrhizobium japonicum USDA 110
       guanine deaminase gene for E. coli"
       /mol_type="unassigned DNA"

<400> SEQUENCE: 4

```
atgactaccg ttggtatccg tggtactttc ttcgacttcg ttgatgaccc gtggaaacac      60
atcggtaacg aacaggctgc tgctcgcttc caccaggacg tctgatggt tgttactgac     120
ggtgttatca aagcgttcgg tccgtacgag aagatcgctg ctgcacaccc gggcgttgaa     180
atcactcaca tcaaagaccg tatcatcgtt ccgggcttca tcgacggtca catccacctg     240
ccgcagactc gcgtactggg tgcttacggt gaacagctgc tgccgtggct gcagaaatct     300
atctacccgg aagagatcaa atacaaagac cgtaactacg cacgtgaagg tgttaagcgc     360
ttcctggatg cgctgctggc agctggtact accacttgcc aggcattcac ttcttcttct     420
ccggttgcaa ctgaagagct gttcgaagaa gcgtctcgcc gtaacatgcg cgttatcgct     480
ggtctgaccg tatcgaccg taacgcaccg gcagaattca tcgacactcc ggaaaacttc     540
taccgtgact ccaagcgtct gatcgctcag taccacgaca aggtcgtaa cctgtacgct     600
atcactccgc gcttcgcatt cggtgcgtct ccggaactgc tgaaagcgtg ccagcgtctg     660
aaacacgaac acccggactg ctgggttaac actcacatct ctgaaaaccc ggcagaatgc     720
tccggcgtac tggttgaaca cccggactgc caggactacc tgggtgttta cgaaaaattc     780
gacctggttg gtccgaaatt ctctggtggt cacggtgttt acctgtctaa caacgaattc     840
cgtcgtatgt ccaagaaagg cgcagctgtt gttttctgcc catgctccaa cctgttcctg     900
ggttctggtc tgttccgtct gggtcgtgcg actgacccgg aacaccgcgt aagatgtcc     960
ttcggtactc acgttggtgg tggtaaccgc ttctccatga tctccgttct ggatgacgct    1020
tacaaagttg gtatgtgtaa caacaccctg ctggatggtt ctatcgaccc gtcccgtaaa    1080
gacctggctg aagctgaacg taacaagctg tctccgtacc gtggcttctg gtctgtaact    1140
ctgggtggtg ctgaaggtct gtacatcgac gacaaactgg gtaacttcga accaggtaaa    1200
gaagctgact cgttgcgct ggatccgaac ggtggtcagc tggcgcagcc gtggcaccag    1260
tctctgatcg ctgacggtgc aggtccgcgt accgttgacg aagcagcttc tatgctgttc    1320
gctgtaatga tggttggtga cgaccgctgc gtagacgaaa cctgggtaat gggtaagcgt    1380
ctgtacaaga aatcc                                                    1395
```

<210> SEQ ID NO 5
<211> LENGTH: 474
<212> TYPE: PRT
<213> ORGANISM: Acidovorax citrulli
<220> FEATURE:
<223> OTHER INFORMATION: Wild type melamine deaminase sequence

<400> SEQUENCE: 5

Met Gln Thr Leu Ser Ile Gln His Gly Thr Leu Val Thr Met Asp Gln
 1               5                  10                  15

Tyr Arg Arg Val Leu Gly Asp Ser Trp Val His Val Gln Asp Gly Arg
                20                  25                  30

Ile Val Ala Leu Gly Val His Ala Glu Ser Val Pro Pro Pro Ala Asp
            35                  40                  45

-continued

Arg Val Ile Asp Ala Arg Gly Lys Val Val Leu Pro Gly Phe Ile Asn
 50                  55                  60

Ala His Thr His Val Asn Gln Ile Leu Arg Gly Gly Pro Ser His
 65                  70                  75                  80

Gly Arg Gln Leu Tyr Asp Trp Leu Phe Asn Val Leu Tyr Pro Gly Gln
                     85                  90                  95

Lys Ala Met Arg Pro Glu Asp Val Ala Val Ala Val Arg Leu Tyr Cys
                100                 105                 110

Ala Glu Ala Val Arg Ser Gly Ile Thr Thr Ile Asn Asp Asn Ala Asp
                115                 120                 125

Ser Ala Ile Tyr Pro Gly Asn Ile Glu Ala Ala Met Ala Val Tyr Gly
130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
                180                 185                 190

Arg Ile Thr Ala Leu Ser Asp Gln Tyr His Gly Thr Ala Gly Gly Arg
                195                 200                 205

Ile Ser Val Trp Pro Ala Pro Ala Ile Thr Pro Ala Val Thr Val Glu
210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Leu His Trp Met
                245                 250                 255

Ser Pro Ala Glu Tyr Met Glu Cys Tyr Gly Leu Leu Asp Glu Arg Leu
                260                 265                 270

Gln Val Ala His Cys Val Tyr Phe Asp Arg Lys Asp Val Arg Leu Leu
                275                 280                 285

His Arg His Asn Val Lys Val Ala Ser Gln Val Val Ser Asn Ala Tyr
                290                 295                 300

Leu Gly Ser Gly Val Ala Pro Val Pro Glu Met Val Glu Arg Gly Met
305                 310                 315                 320

Ala Val Gly Ile Gly Thr Asp Asp Gly Asn Cys Asn Asp Ser Val Asn
                325                 330                 335

Met Ile Gly Asp Met Lys Phe Met Ala His Ile His Arg Ala Val His
                340                 345                 350

Arg Asp Ala Asp Val Leu Thr Pro Glu Lys Ile Leu Glu Met Ala Thr
                355                 360                 365

Ile Asp Gly Ala Arg Ser Leu Gly Met Asp His Glu Ile Gly Ser Ile
                370                 375                 380

Glu Thr Gly Lys Arg Ala Asp Leu Ile Leu Leu Asp Leu Arg His Pro
385                 390                 395                 400

Gln Thr Thr Pro His His His Leu Ala Ala Thr Ile Val Phe Gln Ala
                405                 410                 415

Tyr Gly Asn Glu Val Asp Thr Val Leu Ile Asp Gly Asn Val Val Met
                420                 425                 430

Glu Asn Arg Arg Leu Ser Phe Leu Pro Pro Glu Arg Gly Leu Ala Phe
                435                 440                 445

Leu Glu Glu Ala Gln Ser Arg Ala Thr Ala Ile Leu Gln Arg Ala Asn
450                 455                 460

Met Val Ala Asn Pro Ala Trp Arg Ser Leu

```
            465                 470

<210> SEQ ID NO 6
<211> LENGTH: 109
<212> TYPE: PRT
<213> ORGANISM: Ketogulonicigenium vulgare Y25
<220> FEATURE:
<223> OTHER INFORMATION: Wild type melamine deaminase sequence

<400> SEQUENCE: 6

Met Arg Glu Val Leu Glu Phe Ala Thr Ile Asn Gly Ala Lys Gly Leu
1               5                   10                  15

Arg Leu Asp His Lys Thr Gly Ser Leu Thr Pro Gly Lys Glu Ala Asp
            20                  25                  30

Ile Ile Leu Leu Asp Ala Thr Ala Leu Asn Val Ala Pro Leu Asn Asn
        35                  40                  45

Ala Pro Gly Ala Val Val Thr Leu Met Glu Arg Ser Asn Val Glu Thr
    50                  55                  60

Val Leu Val Ala Gly Gln Ile Lys Lys Trp Gln Gly Ala Leu Ile Gly
65                  70                  75                  80

Gln Asp Ile Ala Ala Leu Arg Asp Gln Ile Ile Ala Ser Arg Asp Tyr
                85                  90                  95

Leu Phe Glu Ala Ala Gly Val Glu Val Pro Leu Phe Asp
            100                 105

<210> SEQ ID NO 7
<211> LENGTH: 477
<212> TYPE: PRT
<213> ORGANISM: Rhodococcus corallinus NRRL B-15444R
<220> FEATURE:
<223> OTHER INFORMATION: Wild type triazine hydrolase sequence

<400> SEQUENCE: 7

Met Thr Arg Ile Ala Ile Thr Gly Gly Arg Val Leu Thr Met Asp Pro
1               5                   10                  15

Glu Arg Arg Val Leu Glu Pro Gly Thr Val Val Glu Asp Gln Phe
            20                  25                  30

Ile Ala Gln Val Gly Ser Pro Thr Thr Ser Ala Ala Pro Lys
        35                  40                  45

Ser Ser Thr Pro Pro Gly Trp Gln Cys Ser Pro Ala Ser Ser Thr Pro
    50                  55                  60

Thr Pro Thr Ser His Lys Ser Ser Ser Gly Val Val His Pro Met Thr
65                  70                  75                  80

Ala Thr Ser Ser Asn Gly Cys Thr Thr Cys Ser Ile Pro Ala Ser Leu
                85                  90                  95

Pro Thr Gln Thr Thr Thr Ser Glu Ser Glu His Cys Cys Thr Ala Pro
            100                 105                 110

Lys Pro Phe Val Leu Ala Ser Pro Leu Ser Ser Thr Thr Arg Thr Ser
            115                 120                 125

Asp Pro Thr Thr Ser Pro Ala Pro Gly Pro Pro Gly Ser Pro Phe Thr
            130                 135                 140

Asp Ala Gly Ile Arg Ala Ile Tyr Ala Arg Met Tyr Phe Asp Ala Pro
145                 150                 155                 160

Arg Ala Glu Leu Glu Glu Leu Val Ala Thr Ile His Ala Lys Ala Pro
                165                 170                 175

Gly Ala Val Arg Met Asp Glu Ser Ala Ser Thr Asp His Val Leu Ala
            180                 185                 190
```

```
Asp Leu Asp Gln Leu Ile Thr Arg His Asp Arg Thr Ala Asp Gly Arg
            195                 200                 205

Ile Arg Val Trp Pro Ala Pro Ala Ile Pro Phe Met Val Ser Glu Lys
    210                 215                 220

Gly Met Lys Ala Ala Gln Glu Ile Ala Ala Ser Arg Thr Asp Gly Trp
225                 230                 235                 240

Thr Met His Val Ser Glu Asp Pro Ile Glu Ala Arg Val His Ser Met
                245                 250                 255

Asn Ala Pro Glu Tyr Leu His His Leu Gly Cys Leu Asp Arg Leu
            260                 265                 270

Leu Ala Ala His Cys Val His Ile Asp Ser Arg Asp Ile Arg Leu Phe
        275                 280                 285

Arg Gln His Asp Val Lys Ile Ser Thr Gln Pro Val Ser Asn Ser Tyr
    290                 295                 300

Leu Ala Ala Gly Ile Ala Pro Val Pro Glu Met Leu Ala His Gly Val
305                 310                 315                 320

Thr Val Gly Ile Gly Thr Asp Asp Ala Asn Cys Asn Asp Ser Val Asn
                325                 330                 335

Leu Ile Ser Asp Met Lys Val Leu Ala Leu Ile His Arg Ala Ala His
            340                 345                 350

Arg Asp Ala Ser Ile Ile Thr Pro Glu Lys Ile Ile Glu Met Ala Thr
        355                 360                 365

Ile Asp Gly Ala Arg Cys Ile Gly Met Ala Asp Gln Ile Gly Ser Leu
    370                 375                 380

Glu Ala Gly Lys Arg Ala Asp Ile Ile Thr Leu Asp Leu Arg His Ala
385                 390                 395                 400

Gln Thr Thr Pro Ala His Asp Leu Ala Ala Thr Ile Val Phe Gln Ala
                405                 410                 415

Tyr Gly Asn Glu Val Asn Asp Val Leu Val Asn Gly Ser Val Val Met
            420                 425                 430

Arg Asp Arg Val Leu Ser Phe Leu Pro Thr Pro Gln Glu Glu Lys Ala
        435                 440                 445

Leu Tyr Asp Asp Ala Ser Glu Arg Ser Ala Ala Met Leu Ala Arg Ala
    450                 455                 460

Gly Leu Thr Gly Thr Arg Thr Trp Gln Thr Leu Gly Ser
465                 470                 475

<210> SEQ ID NO 8
<211> LENGTH: 465
<212> TYPE: PRT
<213> ORGANISM: Bradyrhizobium japonicum
<220> FEATURE:
<223> OTHER INFORMATION: Wild type guanine deaminase sequence

<400> SEQUENCE: 8

Met Thr Thr Val Gly Ile Arg Gly Thr Phe Phe Asp Phe Val Asp
1               5                   10                  15

Pro Trp Lys His Ile Gly Asn Glu Gln Ala Ala Ala Arg Phe His Gln
            20                  25                  30

Asp Gly Leu Met Val Val Thr Asp Gly Val Ile Lys Ala Phe Gly Pro
        35                  40                  45

Tyr Glu Lys Ile Ala Ala Ala His Pro Gly Val Glu Ile Thr His Ile
    50                  55                  60

Lys Asp Arg Ile Ile Val Pro Gly Phe Ile Asp Gly His Ile His Leu
65                  70                  75                  80
```

```
Pro Gln Thr Arg Val Leu Gly Ala Tyr Gly Glu Gln Leu Leu Pro Trp
                85                  90                  95
Leu Gln Lys Ser Ile Tyr Pro Glu Glu Ile Lys Tyr Lys Asp Arg Asn
            100                 105                 110
Tyr Ala Arg Glu Gly Val Lys Arg Phe Leu Asp Ala Leu Leu Ala Ala
        115                 120                 125
Gly Thr Thr Cys Gln Ala Phe Thr Ser Ser Pro Val Ala Thr
130                 135                 140
Glu Glu Leu Phe Glu Glu Ala Ser Arg Arg Asn Met Arg Val Ile Ala
145                 150                 155                 160
Gly Leu Thr Gly Ile Asp Arg Asn Ala Pro Ala Glu Phe Ile Asp Thr
                165                 170                 175
Pro Glu Asn Phe Tyr Arg Asp Ser Lys Arg Leu Ile Ala Gln Tyr His
                180                 185                 190
Asp Lys Gly Arg Asn Leu Tyr Ala Ile Thr Pro Arg Phe Ala Phe Gly
            195                 200                 205
Ala Ser Pro Glu Leu Leu Lys Ala Cys Gln Arg Leu Lys His Glu His
        210                 215                 220
Pro Asp Cys Trp Val Asn Thr His Ile Ser Glu Asn Pro Ala Glu Cys
225                 230                 235                 240
Ser Gly Val Leu Val Glu His Pro Asp Cys Gln Asp Tyr Leu Gly Val
                245                 250                 255
Tyr Glu Lys Phe Asp Leu Val Gly Pro Lys Phe Ser Gly Gly His Gly
                260                 265                 270
Val Tyr Leu Ser Asn Asn Glu Phe Arg Arg Met Ser Lys Lys Gly Ala
            275                 280                 285
Ala Val Val Phe Cys Pro Cys Ser Asn Leu Phe Leu Gly Ser Gly Leu
        290                 295                 300
Phe Arg Leu Gly Arg Ala Thr Asp Pro Glu His Arg Val Lys Met Ser
305                 310                 315                 320
Phe Gly Thr Asp Val Gly Gly Gly Asn Arg Phe Ser Met Ile Ser Val
                325                 330                 335
Leu Asp Asp Ala Tyr Lys Val Gly Met Cys Asn Asn Thr Leu Leu Asp
                340                 345                 350
Gly Ser Ile Asp Pro Ser Arg Lys Asp Leu Ala Glu Ala Glu Arg Asn
            355                 360                 365
Lys Leu Ser Pro Tyr Arg Gly Phe Trp Ser Val Thr Leu Gly Gly Ala
        370                 375                 380
Glu Gly Leu Tyr Ile Asp Asp Lys Leu Gly Asn Phe Glu Pro Gly Lys
385                 390                 395                 400
Glu Ala Asp Phe Val Ala Leu Asp Pro Asn Gly Gly Gln Leu Ala Gln
                405                 410                 415
Pro Trp His Gln Ser Leu Ile Ala Asp Gly Ala Gly Pro Arg Thr Val
                420                 425                 430
Asp Glu Ala Ala Ser Met Leu Phe Ala Val Met Met Val Gly Asp Asp
            435                 440                 445
Arg Cys Val Asp Glu Thr Trp Val Met Gly Lys Arg Leu Tyr Lys Lys
        450                 455                 460
Ser
465

<210> SEQ ID NO 9
<211> LENGTH: 439
<212> TYPE: PRT
```

<213> ORGANISM: Escherichia coli
<220> FEATURE:
<223> OTHER INFORMATION: Wild type Escherichia coli guanine deaminase sequence

<400> SEQUENCE: 9

Met Met Ser Gly Glu His Thr Leu Lys Ala Val Arg Gly Ser Phe Ile
1               5                   10                  15

Asp Val Thr Arg Thr Ile Asp Asn Pro Glu Glu Ile Ala Ser Ala Leu
            20                  25                  30

Arg Phe Ile Glu Asp Gly Leu Leu Leu Ile Lys Gln Gly Lys Val Glu
        35                  40                  45

Trp Phe Gly Glu Trp Glu Asn Gly Lys His Gln Ile Pro Asp Thr Ile
50                  55                  60

Arg Val Arg Asp Tyr Arg Gly Lys Leu Ile Val Pro Gly Phe Val Asp
65                  70                  75                  80

Thr His Ile His Tyr Pro Gln Ser Glu Met Val Gly Ala Tyr Gly Glu
                85                  90                  95

Gln Leu Leu Glu Trp Leu Asn Lys His Thr Phe Pro Thr Glu Arg Arg
            100                 105                 110

Tyr Glu Asp Leu Glu Tyr Ala Arg Glu Met Ser Ala Phe Phe Ile Lys
        115                 120                 125

Gln Leu Leu Arg Asn Gly Thr Thr Thr Ala Leu Val Phe Gly Thr Val
130                 135                 140

His Pro Gln Ser Val Asp Ala Leu Phe Glu Ala Ala Ser His Ile Asn
145                 150                 155                 160

Met Arg Met Ile Ala Gly Lys Val Met Met Asp Arg Asn Ala Pro Asp
                165                 170                 175

Tyr Leu Leu Asp Thr Ala Glu Ser Ser Tyr His Gln Ser Lys Glu Leu
            180                 185                 190

Ile Glu Arg Trp His Lys Asn Gly Arg Leu Leu Tyr Ala Ile Thr Pro
        195                 200                 205

Arg Phe Ala Pro Thr Ser Ser Pro Glu Gln Met Ala Met Ala Gln Arg
210                 215                 220

Leu Lys Glu Glu Tyr Pro Asp Thr Trp Val His Thr His Leu Cys Glu
225                 230                 235                 240

Asn Lys Asp Glu Ile Ala Trp Val Lys Ser Leu Tyr Pro Asp His Asp
                245                 250                 255

Gly Tyr Leu Asp Val Tyr His Gln Tyr Gly Leu Thr Gly Lys Asn Cys
            260                 265                 270

Val Phe Ala His Cys Val His Leu Glu Gly Lys Glu Trp Asp Arg Leu
        275                 280                 285

Ser Glu Thr Lys Ser Ser Ile Ala Phe Cys Pro Thr Ser Asn Leu Tyr
290                 295                 300

Leu Gly Ser Gly Leu Phe Asn Leu Lys Lys Ala Trp Gln Lys Lys Val
305                 310                 315                 320

Lys Val Gly Met Gly Thr Asp Ile Gly Ala Gly Thr Thr Phe Asn Met
                325                 330                 335

Leu Gln Thr Leu Asn Glu Ala Tyr Lys Val Leu Gln Leu Gln Gly Tyr
            340                 345                 350

Arg Leu Ser Ala Tyr Glu Ala Phe Tyr Leu Ala Thr Leu Gly Gly Ala
        355                 360                 365

Lys Ser Leu Gly Leu Asp Asp Leu Ile Gly Asn Phe Leu Pro Gly Lys
370                 375                 380

-continued

Glu Ala Asp Phe Val Val Met Glu Pro Thr Ala Thr Pro Leu Gln Gln
385                 390                 395                 400

Leu Arg Tyr Asp Asn Ser Val Ser Leu Val Asp Lys Leu Phe Val Met
            405                 410                 415

Met Thr Leu Gly Asp Asp Arg Ser Ile Tyr Arg Thr Tyr Val Asp Gly
            420                 425                 430

Arg Leu Val Tyr Glu Arg Asn
        435

<210> SEQ ID NO 10
<211> LENGTH: 1425
<212> TYPE: DNA
<213> ORGANISM: Acidovorax citrulli
<220> FEATURE:
<221> NAME/KEY: source
<222> LOCATION: 1..1425
<223> OTHER INFORMATION: /organism="Acidovorax citrulli"
      /note="Wild type melamine deaminase sequence (triA)"
      /mol_type="unassigned DNA"

<400> SEQUENCE: 10

```
atgcaaacgc tcagcatcca gcacggtacc ctcgtcacga tggatcagta ccgcagagtc     60
cttggggata gctgggttca cgtgcaggat ggacggatcg tcgcgctcgg agtgcacgcc    120
gagtcggtgc ctccgccagc ggatcgggtg atcgatgcac gcggcaaggt cgtgttaccc    180
ggtttcatca tgcccacac ccatgtgaac cagatcctcc tgcgcggagg gccctcgcac    240
gggcgtcaac tctatgactg gctgttcaac gttttgtatc cgggacaaaa ggcgatgaga    300
ccggaggacg tagcggtggc ggtgaggttg tattgtgcgg aagctgtgcg cagcgggatt    360
acgacgatca cgacaacgc cgattcggcc atctacccag gcaacatcga ggccgcgatg    420
gcggtctatg gtgaggtggg tgtgagggtc gtctacgccc gcatgttctt tgatcggatg    480
gacgggcgca ttcaagggta tgtggacgcc ttgaaggctc gctctcccca gtcgaactg    540
tgctcgatca tggaggaaac ggctgtggcc aaagatcgga tcacagccct gtcagatcag    600
tatcatggca cggcaggagg tcgtatatca gtttggcccg ctcctgccat taccccggcg    660
gtgacagttg aaggaatgcg atgggcacaa gccttcgccc gtgatcgggc ggtaatgtgg    720
acgcttcaca tggcggagag cgatcatgat gagcggcttc attggatgag tcccgccgag    780
tacatggagt gttacggact cttggatgag cgtctgcagg tcgcgcattg cgtgtacttt    840
gaccggaagg atgttcggct gctgcaccgc acaatgtga aggtcgcgtc gcaggttgtg    900
agcaatgcct acctcggctc agggtggcc cccgtgccag atggtggga gcgcggcatg    960
gccgtgggca ttgaacaga tgacgggaat tgtaatgact ccgtaaacat gatcggagac   1020
atgaagttta tggcccatat tcaccgcgcg gtgcatcggg atgcggacgt gctgaccccca  1080
gagaagattc ttgaaatggc gacgatcgat ggggcgcgtt cgttgggaat ggaccacgag   1140
attggttcca tcgaaaccgg caagcgcgcg gaccttatcc tgcttgacct gcgtcacccct  1200
cagacgactc ctcaccatca tttggcggcc acgatcgtgt ttcaggctta cggcaatgag   1260
gtggacactg tcctgattga cggaaacgtt gtgatggaga accgccgctt gagctttctt   1320
ccccctgaac gtgagttggc gttccttgag gaagcgcaga gccgcgccac agctattttg   1380
cagcggggcga acatggtggc taacccagct tggcgcagcc tctag                  1425
```

<210> SEQ ID NO 11
<211> LENGTH: 330
<212> TYPE: DNA
<213> ORGANISM: Ketogulonicigenium vulgare Y25

```
<220> FEATURE:
<221> NAME/KEY: source
<222> LOCATION: 1..330
<223> OTHER INFORMATION: /organism="Ketogulonicigenium vulgare Y25"
      /note="Wild type melamine deaminase sequence"
      /mol_type="unassigned DNA"

<400> SEQUENCE: 11
gtgcgcgaag tgctggaatt tgcgacgatc aatggcgcga aaggcctgcg tctggatcac      60
aaaaccggct cgctgacccc cggcaaagag gcggatatca tcctgctgga cgccaccgcc     120
ttgaacgtcg caccgctgaa caacgccccc ggcgccgtcg tgacgctgat ggagcgttcg     180
aacgtggaaa ccgtgctggt cgccggccag atcaagaaat ggcaaggcgc attgatcggt     240
caggatatcg cggcgctgcg cgatcagatc atcgcttcgc gcgattacct gttcgaggca     300
gcgggcgtag aggtgccgct gttcgactaa                                      330

<210> SEQ ID NO 12
<211> LENGTH: 1431
<212> TYPE: DNA
<213> ORGANISM: Rhodococcus corallinus NRRL B-15444R
<220> FEATURE:
<221> NAME/KEY: source
<222> LOCATION: 1..1431
<223> OTHER INFORMATION: /organism="Rhodococcus corallinus NRRL
      B-15444R" /note="Wild type triazine hydrolase sequence "
      /mol_type="unassigned DNA"

<400> SEQUENCE: 12
atgaccagaa tcgcaatcac cggcggacga gtcctgacca tggacccgga gcgccgcgtg      60
ctcgaaccag gaacggttgt ggtcgaggac cagttcatcg cacaagtggg atccccgacg     120
acgtcgacat ccgcggcgcc gaaatcatcg acgccaccgg gatggcagtg ctccccggct     180
tcgtcaacac ccacacccac gtcccacaaa tcctcctcag gggtggtgca tcccatgacc     240
gcaacctcct cgaatggctg cacaacgtgc tctatcccgg cctcgctgcc tacacagacg     300
acgacatccg agtcggaaca ctgctgtact gcgccgaagc ccttcgttct ggcatcacca     360
ctgtcgtcga caacgaggac gtccgaccca cgacttcgc ccgcgccggg gccgccggga     420
tcgcccttca ccgacgcagg aatccgagcc atttacgcgc gcatgtactt cgacgcgcca     480
cgcgccgaac tcgaagaact cgtcgccacc atccacgcca aggcccccgg cgccgtgcgc     540
atggacgaat cagccagcac cgaccacgta ctggcagacc tagaccaact catcacccgc     600
cacgaccgca cagcagatgg ccgcatcagg gtgtggcccg caccgccat ccccttcatg     660 gtcagtgaaa aggaatgaa ggcagcgcaa gagatcgcag cgagccgcac cgacggctgg     720
accatgcacg tcagcgagga tcccatcgag gcccgagtgc actccatgaa cgccccggaa     780
tatttacacc acctcggctg cctcgacgac cgactccttg ccgcgcactg cgtgcatatc     840
gacagccgag acatccgcct gttccgccag cacgacgtaa aaatttctac ccaaccagta     900
tcgaacagct acctggcggc cggaattgca ccggtccccg aaatgctcgc cacggcgtg     960 accgtgggca tcggtaccga cgacgccaac tgcaacgaca gcgtgaacct catctcggac    1020
atgaaagtgc tagcgctcat tcaccgagct gcacatcgag atgcctcaat catcacacct    1080
gaaaaaatca tcgaaatggc caccatcgac ggagcccgct gcatcggtat ggccgatcag    1140
attggttccc tcgaggcggg taaacgcgcc gacatcatca ccctcgacct tgtcacgcc    1200 caaacaaccc cagcgcacga cttggcggcc accatcgtct ttcaggccta cggcaacgag    1260
gtcaacgacg tcctcgtcaa tggctcggta gtgatgcgcg atcgagtact ttctttttctg    1320
```

```
ccgactcccc aagaagaaaa agcgctctac gacgatgcgt cggagcgatc ggctgcaatg      1380
ctcgcacggg ccggcctcac cggcacacgc acatggcaaa cactgggatc g              1431

<210> SEQ ID NO 13
<211> LENGTH: 1398
<212> TYPE: DNA
<213> ORGANISM: Bradyrhizobium japonicum
<220> FEATURE:
<221> NAME/KEY: source
<222> LOCATION: 1..1398
<223> OTHER INFORMATION: /organism="Bradyrhizobium japonicum"
      /note="Wild type guanine deaminase sequence"
      /mol_type="unassigned DNA"

<400> SEQUENCE: 13
atgaccaccg tcggtattcg cggcacgttc ttcgatttcg tcgacgatcc ctggaagcac        60
atcggcaacg agcaggcggc tgcgcgcttt catcaggacg gcctcatggt cgtcaccgac       120
ggcgtcatca aggcgttcgg tccgtacgag aagatcgccg ccgcgcatcc gggcgttgag       180
atcacccata tcaaggaccg catcatcgtc ccgggcttca tcgacggcca catccatctg       240
cctcagaccc gcgtgctcgg tgcctatggc gagcagctct tgccgtggct gcagaagtcg       300
atctatcccg aggagatcaa gtacaaggat cgcaactacg cgcgcgaagg cgtgaagcgt       360
tttctcgatg cactgctcgc cgccggcacc accacctgcc aggccttcac cagctcctca       420
ccggtcgcga ccgaagagct gttcgaggag caagcaggc gcaacatgcg cgtgatcgcg        480
ggtctcaccg ggatcgaccg caacgcgccg gccgaattca tcgatacgcc cgagaatttc       540
tatcgcgaca gcaagcggct gatcgcgcag tatcacgaca agggccgtaa cctctacgct       600
atcacgccgc gcttcgcctt cggcgcctcg cccgagctgc tgaaggcgtg tcagcgcctc       660
aagcacgagc atccggactg ctgggtcaat acccacatct ccgagaaccc ggccgaatgc       720
agcggcgtgc tggtcgagca cccggactgc caggattatc tcggcgtcta cgagaagttc       780
gacctggtcg gcccaaagtt ctccggcggc cacggcgtct atctctcgaa caacgaattc       840
cgccgcatgt ccaagaaagg cgcggcggta gtgttctgcc cgtgctcgaa cctgttcctc       900
ggcagcggcc tgttccgtct cggccgcgcc accgatccgg agcatcgcgt gaagatgtcg       960
ttcggcaccg atgtcggcgg cggcaaccgc ttctcgatga tctccgtgct cgacgacgct      1020
tacaaggtcg gcatgtgcaa caacacgctg ctcgacggca gcatcgatcc gtcgcgcaag      1080
gacctcgcgg aagccgagcg caacaagctc tcgccctatc gtggcttctg gtcggtcacg      1140
ctcgcgggcg ccgaaggcct ctacatcgac gacaagctcg gcaatttcga gcccggcaag      1200
gaggccgatt tcgtcgcgct cgatccgaac ggcggacaac tggcgcaacc ctggcaccag      1260
tcgctgattg ccgacggtgc aggtccgcgc acggttgatg aggccgcgag catgctgttc      1320
gccgtcatga tggtcggcga cgatcgctgc gtcgacgaga cctgggtgat gggcaagcgc      1380
ctctacaaga agagctga                                                    1398

<210> SEQ ID NO 14
<211> LENGTH: 1317
<212> TYPE: DNA
<213> ORGANISM: Escherichia coli
<220> FEATURE:
<221> NAME/KEY: source
<222> LOCATION: 1..1317
<223> OTHER INFORMATION: /organism="Escherichia coli"
      /note="Wild type Escherichia coli guanine deaminase sequence"
      /mol_type="unassigned DNA"

<400> SEQUENCE: 14
```

```
atgatgtcag gagaacacac gttaaaagcg gtacgaggca gttttattga tgtcacccgt      60
acgatcgata acccgaaga gattgcctct gcgctgcggt ttattgagga tggtttatta     120
ctcattaaac agggaaaagt ggaatggttt ggcgaatggg aaaacggaaa gcatcaaatt     180
cctgacacca ttcgcgtgcg cgactatcgc ggcaaactga tagtaccggg ctttgtcgat     240
acacatatcc attatccgca aagtgaaatg gtggggcct atggtgagca attgctggag     300
tggttgaata aacacacctt ccctactgaa cgtcgttatg aggatttaga gtacgcccgc     360
gaaatgtcgg cgttcttcat caagcagctt ttacgtaacg gaaccaccac ggcgctggtg     420
tttggcactg ttcatccgca atctgttgat gcgctgtttg aagccgccag tcatatcaat     480
atgcgtatga ttgccggtaa ggtgatgatg gaccgcaacg caccggatta tctgctcgac     540
actgccgaaa gcagctatca ccaaagcaaa gaactgatcg aacgctggca caaaaatggt     600
cgtctgctat atgcgattac gccacgcttc gccccgacct catctcctga acagatggcg     660
atggcgcaac gcctgaaaga agaatatccg gatacgtggg tacataccca tctctgtgaa     720
aacaaagatg aaattgcctg ggtgaaatcg ctttatcctg accatgatgg ttatctggat     780
gtttaccatc agtacggcct gaccggtaaa aactgtgtct ttgctcactg cgtccatctc     840
gaagaaaaag agtgggatcg tctcagcgaa accaaatcca gcattgcttt ctgtccgacc     900
tccaaccttt acctcggcag cggcttattc aacttgaaaa aagcatggca gaagaaagtt     960
aaagtgggca tgggaacgga tatcggtgcc ggaaccactt tcaacatgct gcaaacgctg    1020
aacgaagcct acaaagtatt gcaattacaa ggctatcgcc tctcggctta tgaagcgttt    1080
tacctggcca cgctcggcgg agcgaaatct ctgggccttg acgatttgat tggcaactt    1140 ttacctggca aagaggctga tttcgtggtg atggaaccca ccgccactcc gctacagcag    1200
ctgcgctatg acaactctgt ttctttagtc gacaaattgt tcgtgatgat gacgttgggc    1260
gatgaccgtt cgatctaccg cacctacgtt gatggtcgtc tggtgtacga acgcaac      1317
```